United States Patent [19]

Bengtsson et al.

[11] Patent Number: 5,690,960

[45] Date of Patent: Nov. 25, 1997

[54] PHARMACEUTICAL FORMULATION OF OMEPRAZOLE

[75] Inventors: Inga Siv Bengtsson, Göteborg; Kurt Ingmar Lövgren, Mölnlycke, both of Sweden

[73] Assignee: Astra Aktiebolag, Sodertalje, Sweden

[21] Appl. No.: 313,036

[22] PCT Filed: Jul. 8, 1994

[86] PCT No.: PCT/SE94/00681

§ 371 Date: Sep. 27, 1994

§ 102(e) Date: Sep. 27, 1994

[87] PCT Pub. No.: WO95/01783

PCT Pub. Date: Jan. 19, 1995

[30] Foreign Application Priority Data

Jul. 9, 1993 [SE] Sweden .................. 9302395

[51] Int. Cl.[6] .................. A61K 9/32; A61K 9/36
[52] U.S. Cl. .................. 424/480; 424/474; 424/482; 424/494; 424/497
[58] Field of Search .................. 424/480, 474, 424/482, 494, 497

[56] References Cited

U.S. PATENT DOCUMENTS

| | | | |
|---|---|---|---|
| 4,738,974 | 4/1988 | Brandstrom | 514/338 |
| 4,786,505 | 11/1988 | Lovgren et al. | 424/468 |

FOREIGN PATENT DOCUMENTS

| | | |
|---|---|---|
| 0005129 | 4/1981 | European Pat. Off. . |
| 0124495 | 11/1984 | European Pat. Off. . |
| 0342522 | 11/1989 | European Pat. Off. . |
| 0247983 | 12/1990 | European Pat. Off. . |
| 9501783 | 8/1994 | WIPO . |

OTHER PUBLICATIONS

Pilbrant et al., "Development of an oral formulation of omeprazole," Scand J Gastroenterol 1985; vol. 20 (Suppl 108) : 113–120.

Primary Examiner—Thurman K. Page
Assistant Examiner—James M. Spear
Attorney, Agent, or Firm—White & Case

[57] ABSTRACT

A new oral pharmaceutical formulation containing a novel physical form of a magnesium salt of omeprazole, a method for the manufacture of such a formulation, and the use of such a formulation in medicine.

22 Claims, No Drawings

5,690,960

PHARMACEUTICAL FORMULATION OF OMEPRAZOLE

This application is a 371 of PCT/SE 94/00681 filed Jul. 8, 1994.

FIELD OF THE INVENTION

The present invention is related to a new pharmaceutical formulation containing a novel physical form of a magnesium salt of omeprazole, to a method for the manufacture of such a formulation, and to the use of such a formulation in medicine.

BACKGROUND OF THE INVENTION

The compound known under the generic name omeprazole, 5-methoxy-2(((4-methoxy-3,5-dimethyl-2-pyridinyl)methyl)sulfinyl)-1H-benzimidazole, is described i.a. in EP-A 0 005 129.

Omeprazole is useful for inhibiting gastric acid secretion and has gastric mucosa protective activity. In a more general sense, omeprazole may be used for prevention and treatment of gastric acid related disorders in mammals and man, including e.g. gastroesofageal reflux disease, gastritis, gastric ulcer and duodenal ulcer. Omeprazole is susceptible to degradation/transformation in acid reacting and neutral media. The half-life of degradation of omeprazole in water solutions at pH-values less than four is shorter than ten minutes. Also at neutral pH-values degradation proceeds rapidly, e.g. at pH=7 the half-life of omeprazole is about 14 hours, while at higher pH-values the stability in solution is much better (Pilbrant and Cederberg, Scand. J. Gastroenterology 1985; 20 (suppl. 108) p. 113–120). Omeprazole also in the solid state is susceptible to degradation and is stabilized in mixtures with alkaline reacting compounds. The stability of omeprazole is also affected by moisture, heat, organic solvents and to some degree by light.

From what is said about the stability properties of omeprazole, it is obvious that an oral dosage form of omeprazole must be protected from contact with the acid reacting gastric juice and the active substance must be transferred in intact form to that part of the gastrointestinal tract where pH is near neutral and where rapid absorption of omeprazole can occur.

A pharmaceutical oral solid dosage form of omeprazole must be protected from contact with acidic gastric juice by an enteric coating. In U.S. Pat. No. 4,786,505 is described an enteric coated omeprazole preparation containing a separating subcoat between the core material and the enteric coating. Said preparation contains an alkaline core comprising omeprazole, a subcoating and an enteric coating.

Certain salts of omeprazole including alkaline reacting salts of omeprazole are described in EP-A 0 124 495. In said patent specification the requirements and importance regarding storage stability of omeprazole for incorporation in pharmaceutical preparations are emphasized.

There is however, a demand for the development of new enteric preparations of omeprazole with enhanced stability and for environmental aspects there is also a strong desire for the use of water based processes in production of pharmaceutical products.

The isolation and purification in full manufacturing scale of the magnesium omeprazole salts described in EP-A 0 124 495 presents one major problem in that the magnesium omeprazole salt particles are very fragile making pharmaceutical manufacturing processes utilising this product less attractive in full scale production. Performing the process without crystallization of the magnesium omeprazole gives a product which is less suitable as a pharmaceutical substance.

In order to use the magnesium salt of omeprazole, in this specification denoted magnesium omeprazole, in full manufacturing scale in preparing pharmaceutical formulations primarily for oral administration, such as tablets, it is necessary that said magnesium omeprazole possesses a combination of properties which makes such full scale manufacturing feasible.

The combination of physical properties of the novel magnesium omeprazole product described in the present specification with respect to the degree of crystallinity, particle diameter, density, hygroscopicity, low water content and low content of other solvents is favorable and permits the manufacture of magnesium omeprazole in a form which is useful for the manufacture of the new pharmaceutical formulation.

The novel form of magnesium omeprazole can be formulated into different dosage forms for oral and rectal administration. Examples of such formulations are tablets, granules, pellets, capsules, suppositories and suspensions.

SUMMARY OF THE INVENTION

One object of the present invention is to provide a pharmaceutical formulation of magnesium omeprazole.

Another object of the present invention is to provide a process for full scale production of pharmaceutical formulations of omeprazole, especially an enteric coated dosage form of omeprazole, which is resistant to dissolution in acid media and which dissolves rapidly in neutral to alkaline media and has a good stability during long-term storage.

Yet another object of the invention is to provide an environment friendly completely water-based process for the manufacture of pharmaceutical formulations of omeprazole.

The new dosage form is characterized in the following way. Core material in the form of pellets, granules or tablets containing the novel form of a magnesium salt of omeprazole, optionally together with an alkaline reacting compound, and on said core material one or more subcoating layers optionally comprising tablet excipients which are soluble or insoluble but disintegrating in water, or polymeric, filmforming compounds, optionally containing pH-buffering, alkaline compounds between the core and an outer layer, which is an enteric coating. This/these inner layer/layers separates/separate the core material from the outer layer being an enteric coating.

The process of forming the enteric coated dosage form is preferably water-based. Also the enteric coating process step, which usally is carried out using an organic solvent, can be carried out using a water-based process which is desirable both for the working environment inside the pharmaceutical plant and for global environmental reasons.

It has been found that a magnesium omeprazole having a degree of crystallinity which is higher than 70% is useful in the manufacture of the pharmaceutical formulations of omeprazole according to the present invention.

DETAILED DESCRIPTION OF THE INVENTION

The new pharmaceutical formulation is defined in claims 1–8, a process for the manufacture of the pharmaceutical formulation according to the present invention is defined in claims 9–10 and the use of the formulation in medicine is defined in claims 11–17.

Magnesium Omeprazole

Magnesium omeprazole feasible for the manufacturing of the claimed formulation has the following properties:

a) Crystalline form, with a degree of crystallinity of not less than 70%, preferably higher than 75% as determined by X-ray powder diffraction It is desirable that the product also exhibits the following properties;

b) Particle size measured as mean mass diameter (MMD) less than 30 μm, preferably less than 20 μm as determined by laser diffraction technique.

c) Density between 1.33 g/cm$^3$ and 1.35 g/cm$^3$ as determined by powder pycnometer.

d) Hygroscopicity not exceeding 2% increase of weight upon storage for one month up to 94% relative atmospheric humidity as determined gravimetrically.

e) A content of water of between 5% and 10% by weight as determined by titration according to Karl Fischer.

f) A content of methanol less than 0.1% preferably less than 0.05% by weight as determined by gas chromatography, in case methanol is used as solvent.

The process for producing the novel form of magnesium omeprazole is characterized by the following consecutive steps 1) treating omeprazole or a salt thereof with magnesium alcoholate in a solution
2) separating inorganic salts from the reaction mixture
3) crystallizing magnesium omeprazole
4) isolating the obtained crystalline magnesium omeprazole and, optionally
5) purifying and drying the crystalline magnesium omeprazole using conventional methods.

The process for manufacturing the novel magnesium omeprazole can be described in the following way:

A lower alcohol, such as methanol, ethanol, n-propanol or iso-propanol, preferably methanol, is treated in a solution of polar solvents with a weighed amount of magnesium at temperatures between 0° C. and reflux temperature. The temperature should preferably be between 10° and 30° C. After addition of the magnesium to the solution the temperature can, in a second step be raised further to between 0° C. and reflux temperature, preferably 20°–50° C. After termination of the reaction the temperature is reduced to 0°–40° C., preferably 10°–25° C. Omeprazole or a salt of omeprazole is then added to the solution and after termination of the reaction the mixture is cooled to −10° C. to +20° C., preferably −5° C. to +5° C. The solvent is then evaporated to 40–60% of the initial volume, which makes the inorganic salts precipitate. The precipitate is separated from the reaction solution for example by centrifugation or filtration and the solution is heated to 5° C. to 30° C. whereafter the solution is seeded with magnesium omeprazole crystals. An amount of water, which is approximately equal to the volume of the solution, is added to start the crystallization. The solution is cooled to −10°to +20° C., preferably 0°–10° C. to complete the crystallization. The crystals are then separated from the mother liquid for example by centrifugation or filtration and washed with polar solvents preferably an aqueous lower alcohol such as aqueous methanol. Finally, the crystals are dried preferably under reduced pressure and heating.

Pharmaceutical formulations containing the novel magnesium omeprazole described above are manufactured as described herein below.

Core Material

The novel magnesium salt of omeprazole, herein referred to as magnesium omeprazole, is mixed with inert, preferably water soluble, conventional pharmaceutical constituents to obtain the preferred concentration of omeprazole in the final mixture. Optionally the magnesium omeprazole may be mixed with an alkaline reacting, otherwise inert, pharmaceutically acceptable substance (or substances). Such substances can be chosen among, but are not restricted to substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar compounds; organic pH-buffering substances such as trihydroxymethylaminomethane, basic amino acids and their salts or other similar, pharmaceutically acceptable pH-buffering substances.

The powder mixture is then formulated into pellets, granules or tablets, by conventional pharmaceutical procedures. The pellets, granules or tablets are used as core material for further processing.

Separating Layer—Subcoating

The cores containing magnesium omeprazole and optionally alkaline reacting substances are separated from the enteric coating polymer(s). The subcoating layer, in the following defined as the separating layer, serves as a pH-buffering zone in which hydrogen ions diffusing from the outside in towards the core can react with hydroxyl ions diffusing from the core towards the surface of the coated particles. The pH-buffering properties of the separating layer can be further strengthened by introducing in the layer substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO.CO_2.12H_2O$, $(Mg_6Al_2(OH)_{16}CO_3.4H_2O)$, $MgO.Al_2O_3.2SiO_2.nH_2O$, aluminium hydroxide/sodium bicarbonate coprecipitate or similar compounds; or other pharmaceutically acceptable pH-buffering compounds such as, for instance the sodium, potassium, calcium, magnesium and aluminium salts of phosphoric, carbonic, citric or other suitable, weak, inorganic or organic acids; or suitable organic bases, including basic amino acids or salts thereof.

The separating layer may consist of one or more layers.

The separating layer(s) can be applied to the core material—pellets, granules or tablets—by conventional coating procedures in a suitable coating pan, centrifugal fluidized coating-granulator, or in a fluidized bed apparatus using water and/or conventional organic solvents for the coating solution. The material for the separating layer is chosen among pharmaceutically acceptable, inert compounds or polymers used for film-coating applications such as, for instance, sugar, polyethylene glycol, polyvinylpyrrolidone, polyvinyl alcohol, hydroxypropyl cellulose, methylcellulose, ethylcellulose, hydroxymethyl cellulose or hydroxypropyl methylcellulose. The separating layer, "subcoating", applied to the core material may constitute from approximately 0.5 to 25% by weight of the core weight, preferably 2.0–10.0%, and more preferably 2.5–5.0%.

In the case of a tablet formulation another method to apply the separating layer(s) can be performed by drycoating technique. First a tablet containing magnesium omeprazole is formulated as described above. Around this tablet one or more layers are compressed using a suitable tableting machine. The separating layer(s) consists of pharmaceutically acceptable, soluble or insoluble but in water disintegrating tablet excipients. The separating layer(s) has preferably a thickness of not less than approximately 1 mm.

Ordinary plasticizers, colorants, pigments, titanium dioxide, talc and other additives may also be included into one or more of the separating layer(s).

Enteric Coating Layer

The enteric coating layer is applied in one or more layers onto the subcoated core material by conventional coating techniques such as, for instance, pan coating or fluidized bed coating using solutions of polymers in water, or by using latex suspensions of said polymers or optionally using polymer solutions in suitable organic solvents. As enteric coating polymers can be used one or more of the following, for example solutions or dispersions of acrylates (methacrylic acid/methacrylic acid methylester copolymer), cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s). Preferably water-based polymer dispersions such as for example compounds known under the trade names Aquateric® (FMC Corporation), Eudragit® (Röhm Pharma), Aqoat™ (Shin-Etsu Chemical), Opadry™ (Colorcon) or similar compounds are used to obtain enteric coatings. The enteric coating layer can optionally contain a pharmaceutically acceptable plasticizer for example cetanol, triacetin, citric acid esters such as, those known under the trade name Citroflex® (Pfizer), phthalic acid esters, dibutyl succinate, polyethylene glycol (PEG) or similar plasticizers. The amount of plasticizer is usually optimized for each enteric coating polymer(s) and is usually in the range of 1–50% of the enteric coating polymer(s). Dispersants such as talc, colorants and pigments may also be included into the enteric coating layer or sprayed onto the enteric coated material as an overcoat.

The thickness of the enteric coating may vary widely without influencing the in vitro release of omeprazole in test solutions which mimic in vivo conditions in man. To protect the acid susceptible omeprazole compound and to obtain an acceptable acid resistance, the enteric coating constitutes at least an amount of 1.0% by weight of the core weight, preferably at least 3.0% and especially at least 6.0%. The upper amount of the applied enteric coating is normally only limited by processing conditions. This possibility to vary the thickness of the enteric coating without deleterious influence on the release of omeprazole is especially desirable in large scale processes. The enteric coating layer(s) may be applied on the pre-processed formulation containing subcoating layer(s) without exactly controlling the thickness of the applied coating layer(s).

Thus, the formulation according to the invention consists of core material containing magnesium omeprazole optionally mixed with alkaline reacting compound(s). The addition of alkaline reacting material is not necessary, in any sense, but such a substance may further enhance the stability of omeprazole. The core material is coated with an enteric coating rendering the dosage form insoluble in acid media, but disintegrating/dissolving in neutral to alkaline media such as, for instance the liquids present in the proximal part of the small intestine, the site where dissolution is wanted. The core material is further coated with an soluble or insoluble but in water disintegrating coating, optionally containing one or more pH-buffering substances, which separate the core material from the enteric coating.

Final Dosage Form

The final dosage form is either an enteric coated tablet or capsule or in the case of enteric coated pellets or granules, these pellets or granules dispensed in hard gelatin capsules or sachets. The final dosage form may further be coated with an additional layer containing pigment(s) and/or colorant(s). It is essential for the long term stability during storage that the water content of the final dosage form containing magnesium omeprazole (enteric coated tablets, capsules, granules or pellets) is kept low.

Process

A process for the manufacture of a dosage form according to the present invention represents a further aspect of the invention. After the forming of the core material, said material is first coated with the separating layer(s) and then with the enteric coating layer(s). The coating(s) are carried out as described above. Further another aspect of the invention is that the pharmaceutical processes can be completely water-based.

The preparation according to the invention is especially advantageous in reducing gastric acid secretion. It is administered one to several times a day. The typical daily dose of the active substance varies and will depend on various factors such as the individual requirements of the patients, the mode of administration and the disease. In general the daily dose will be in the range of 1–400 mg of omeprazole.

The invention is illustrated in detail by the following examples. Example 1 discloses the preparation of the novel magnesium omeprazole product, which product is suitable in manufacturing of the pharmaceutical formulations according to the present invention. Example 2 discloses compositions of different enteric coated tablets containing magnesium omeprazole and results from acid resistance test and in vitro dissolution test. Examples 3 discloses tablet formulations with different thickness of the enteric coating, the obtained gastric acid resistance of said formulations and the in vitro release rate of omeprazole. Example 4 discloses an enteric coated pellet formulation.

EXAMPLES

The following detailed Example 1 will serve to illustrate a process for manufacturing the magnesium omeprazole, which will be used in the pharmaceutical preparations according to the present invention.

Example 1

A reactor was filled with 2026 liters of methanol. The stirrer was started and the temperature was adjusted to 20° C. 3,90 kg of magnesium was added to the vessel and immediately thereafter 1,0 liter of $CH_2Cl_2$. The reactor was heated to 40° C. and kept at this temperature for 60 min. It was then cooled to 15° C. before the addition of 99,9 kg of omeprazole. The reactor was kept at this temperature for 60 min and then cooled to 0° C. The temperature was kept at this level for 30 minutes before 1000 L of methanol were evaporated under vacuum and the inorganic solid salt was separated from the liquid first by centrifugation and then by filtration. The liquid was heated to 10° C. and the liquid was seeded with magnesium omeprazole crystals whereafter the magnesium omeprazole salt was precipitated by addition of 900 L of water. The mixture was then cooled to 5° C. After the crystallization had been completed the magnesium omeprazole crystals were centrifuged off and then washed with a mixture of 50 L of methanol and 150 L of water. The produced magnesium omeprazole was dried under reduced pressure finally producing 92,5 kg of crystalline product corresponding to a yield of 81,4%.

The novel form of the magnesium salt of omeprazole according to Example 1 fulfills the properties defined above.

Example 2

Tablet formulations containing magnesium omeprazole.

| Amount omeprazole<br>Ingredient | 10<br>(mg/tabl) | 20<br>(mg/tabl) | 40<br>(mg/tabl) |
|---|---|---|---|
| Tablet core | | | |
| Magnesium omeprazole | 11.2 | 22.5 | 45.0 |
| Mannitol | 68.7 | 57.4 | 34.9 |
| Microcrystalline cellulose | 25.0 | 25.0 | 25.0 |
| Sodium starch glycolate | 6.0 | 6.0 | 6.0 |
| Hydroxypropyl methylcellulose | 6.0 | 6.0 | 6.0 |
| Talc | 5.0 | 5.0 | 5.0 |
| Sodium stearyl fumarate | 2.5 | 2.5 | 2.5 |
| Water purified | 50.0 | 50.0 | 50.0 |
| Sub-coating layer | | | |
| Hydroxypropyl methylcellulose | 3.7 | 3.7 | 3.7 |
| Hydrogen peroxide 30% | 0.04 | 0.04 | 0.04 |
| Water purified | 34.0 | 34.0 | 34.0 |
| Enteric coating layer | | | |
| Methacrylic acid copolymer | 9.1 | 9.1 | 9.1 |
| Polyethylene glycol | 1.0 | 1.0 | 1.0 |
| Titanium dioxide | 0.82 | 1.1 | 0.51 |
| Colour iron oxide, red-brown | 0.04 | 0.13 | 0.43 |
| Colour iron oxide, yellow | 0.02 | — | — |
| Water purified | 45.0 | 45.0 | 45.0 |
| Polish | | | |
| Paraffin powder | 0.05 | 0.05 | 0.05 |

The tablets with an amount of 20 mg omeprazole/tablet have been manufactured both in a pilot scale of about 300 000 tablets and a large scale of about 2 million tablets.

Description of Manufacturing

Magnesium omeprazole, mannitol, hydroxypropyl methylcellulose, microcrystalline cellulose and sodium starch glycolate are dry-mixed, moistened with water and wet mixed. The wet mass is dried and milled and finally mixed with anti-adherent and lubricant substances. The milled granulate is compressed to tablets with a diameter of 7 mm. The tablets are sub-coated with a polymer film based on hydroxypropyl methylcellulose and enteric coated with a methacrylic acid copolymer film. Water used in the manufacture of the tablets is removed during subsequent processing.

Investigation of Acid-Resistance

Six individual tablets were exposed to artificial gastric fluid without enzymes, pH 1.2. After six hours the tablets were removed, washed and analysed for omeprazole content using HPLC. The amount of omeprazole is taken as acid resistance.

| Tablet Strength<br>(mg) | Acid resistance<br>(%) |
|---|---|
| 10 | 95 (93–98) |
| 20 | 100 (94–102) |
| 40 | 100 (96–103) |

Investigation of In-Vitro Dissolution

After exposure to acid environment, pH 1.2, as described above, the medium was switched to artificial intestinal fluid without enzymes, pH 6.8. The dissolved amount of omeprazole was determined by HPLC.

| Tablet | Dissolved amount of omeprazole (%) after (minutes) | | | | | | |
|---|---|---|---|---|---|---|---|
| Strength<br>(mg) | 0<br>(%) | 5<br>(%) | 10<br>(%) | 15<br>(%) | 20<br>(%) | 25<br>(%) | 30<br>(%) |
| 10 | 0 | 2 | 78 | 92 | 93 | 94 | 94 |
| 20 | 0 | 0 | 75 | 93 | 96 | 96 | 97 |
| 40 | 0 | 9 | 71 | 86 | 91 | 91 | 94 |

All values of dissolved amount of omeprazole are mean values of 12 tablets.

Example 3

Tablet formulations containing magnesium omeprazole with different thickness of the enteric coating.

The composition of the tablets is the same as in Example 2 (20 mg omeprazole). The tablets (n=6) have been exposed in an artificial gastric juice (pH 1.2) during 2 hours and then analysed for remaining amount of omeprazole (acid resistance). The release of omeprazole was analysed on tablets (n=6) pre-exposed in gastric juice 2 hrs and thereafter exposed in a buffer solution (pH 6.8) during 30 min.

| Experiment*) | Enteric coating<br>(% weight per tablet) | Acid resistance<br>(% residue after 2 h; pH 1.2) | Release<br>(% after 30 min; pH 6.8) |
|---|---|---|---|
| A | 8 | 101 (98–105) | 94 (93–96) |
| B | 8 | 100 (98–102) | 95 (85–98) |
| C | 16 | | 98 (96–100) |

*)A manufactured in large scale
B manufactured in pilot scale
C manufactured in laboratory scale

Example 4

Enteric coated pellet formulation containing magnesium omeprazole.

| Pellet core | |
|---|---|
| Magnesium omeprazole | 225 g |
| Mannitol | 1425 g |
| Hydroxypropyl cellulose | 60 g |
| Microcrystalline cellulose | 40 g |
| Lactose anhydrous | 80 g |
| Sodium lauryl sulphate | 5 g |

| | |
|---|---|
| Disodium hydrogen phosphate dihydrate | 8 g |
| Water purified | 350 g |
| Subcoating layer (I) | |
| Hydroxypropyl methylcellulose | 70 g |
| Water purified | 1450 g |
| Enteric-coating layer (II) | |
| Methacrylic acid copolymer | 430 g |
| Polyethylene glycol | 40 g |
| Water purified | 1890 g |
| Polish | |
| Magnesium stearate | 5 g |

The dry ingredients given above were mixed well in a mixer. Addition of granulation liquid was made and the mixture was kneaded and granulated to a proper consistency. The wet mass was pressed through an extruder and the granules were converted to spherical form in a spheronizer. The pellets were dried and classified into suitable particle size ranges, e.g. 0.5–1.5 mm.

The polymer solution (I) was sprayed on the uncoated pellets in a fluidized bed apparatus under conditions suitable for the equipment used.

The polymer dispersion (II) was sprayed on the subcoated pellets in a fluidized bed apparatus. The enteric-coated pellets were classified, polishing material was admixed and the pellets were filed into hard gelatin capsules in an amount corresponding to 20 mg of omeprazole, using a capsule filling machine.

Biopharmaceutical Tests

The enteric coated formulations according to Example 2 have been tested in humans with good results.

We claim:

1. A stable oral formulation comprising:
   a core containing a magnesium salt of omeprazole said salt having more than 70% crystallinity as determined by x-ray powder diffraction;
   a subcoating layer; and
   an enteric coating layer, whereby the thickness of the enteric coating layer does not effect the release of omeprazole into solution at the pH predominantly present in the small intestine.

2. A formulation according to claim 1, wherein the formulation is a tablet formulation.

3. A formulation according to claim 1, wherein the formulation is a pellet formulation.

4. A formulation according to claim 1, wherein the enteric coating comprising an enteric coating material, optionally containing one or more pharmaceutically acceptable plasticizers, dispersants, colorants and pigments.

5. A formulation according to claim 4, wherein the enteric coating comprises water-based polymer solutions or dispersions of acrylates, hydroxypropyl methylcellulose acetate succinate, hydroxypropyl methylcellulose phthalate, polyvinyl acetate phthalate, cellulose acetate trimellitate and/or cellulose acetate phthalate.

6. A formulation according to claim 1, wherein the enteric coating constitutes from 1.0% by weight of the weight of the core material.

7. A formulation according to claim 6, wherein the enteric coating constitutes at least 3.0% by weight of the weight of the core material.

8. A formulation according to claim 1 wherein the sub-coating layer(s) comprise polymeric, filmforming compounds or tablet excipients which are soluble or insoluble but disintegrating in water, and optionally containing pH-buffering, alkaline compounds.

9. A formulation according to claim 1 wherein the produced enteric coated formulation contains an overcoat, optionally comprising one or more pharmaceutically acceptable plasticizers, dispersants, colorants and pigments.

10. A process for the manufacture of a formulation of a pharmaceutical composition for the oral administration of magnesium omeprazole comprising the steps of:
   (a) forming a core material containing magnesium omeprazole salt said salt having at least 70% crystallinity as determined by x-ray powder diffraction;
   (b) applying in the presence of water at least one subcoating layer onto the core;
   (c) further applying in the pittance of water at least one enteric coating layer onto the subcoated core; and drying the prepared formulation.

11. A process according to claim 10, wherein the subcoating layer(s) is applied on the core material by a dry-coating process.

12. The oral formulation according to claim 8 or 1 wherein the core is coated with more than one subcoating layer.

13. The oral formulation according to any one of the claim 1, 4–7 or 9 wherein the enteric coating comprises more than one layer.

14. The oral formulation according to claim 1 wherein the crystalline magnesium omeprazole has a mean mass particle size diameter of less than 30 μm.

15. The oral formulation according to claim 1 wherein the crystalline magnesium omeprazole has a hygroscopicity of less than 2% by weight.

16. The formulation according to claim 1, wherein the core material is in the form of pellets, granules or tablets.

17. A method for inhibiting gastric acid secretion in mammals and man by administering to a host in need thereof a therapeutically effective dose of an enteric coated formulation according to any of claims 1 to 9.

18. A method for the treatment of gastric acid related diseases in mammals and man by administering to a host in need thereof a therapeutically effective dose of an enteric coated formulation according to any of claims 1 to 9.

19. The formulation according to claim 1, wherein the core further comprises an alkaline reacting compound.

20. The process according to claim 10, wherein the core material further comprises an alkaline reacting compound.

21. A pharmaceutical composition produced in accordance with the process of claim 10.

22. An improved oral pharmaceutical composition containing a core of omeprazole salt with a subcoating and an enteric coating wherein the improvement comprises magnesium omeprazole salt having more than 70% crystallinity as determined by x-ray powder diffraction.

* * * * *

UNITED STATES PATENT AND TRADEMARK OFFICE
CERTIFICATE OF CORRECTION

PATENT NO.    : 5,690,960
DATED         : November 25, 1997
INVENTOR(S)   : Bengtsson et al.

It is certified that error appears in the above-indentified patent and that said Letters Patent is hereby corrected as shown below:

col. 9, line 43 (claim 1, line 7), change "effect" to --significantly affect--;

col. 10, line 22, change "pittance" to --presence--;

col. 10, lines 31, change "claim" to --claims--.

Signed and Sealed this

Second Day of June, 1998

*Attest:*

BRUCE LEHMAN

*Attesting Officer*     Commissioner of Patents and Trademarks